US008540983B2

(12) United States Patent
Gorecki et al.

(10) Patent No.: US 8,540,983 B2
(45) Date of Patent: *Sep. 24, 2013

(54) DEBRIDING COMPOSITION FROM BROMELAIN AND METHODS OF PRODUCTION THEREOF

(75) Inventors: Marian Gorecki, Tel Aviv (IL); Amir Toren, Raanana (IL)

(73) Assignee: MediWound Ltd., Yavne (IL)

( * ) Notice: Subject to any disclaimer, the term of this patent is extended or adjusted under 35 U.S.C. 154(b) by 29 days.

This patent is subject to a terminal disclaimer.

(21) Appl. No.: 13/366,954

(22) Filed: Feb. 6, 2012

(65) Prior Publication Data

US 2012/0171187 A1  Jul. 5, 2012

Related U.S. Application Data

(63) Continuation of application No. 11/719,586, filed as application No. PCT/IL2005/001236 on Nov. 22, 2005, now Pat. No. 8,119,124.

(30) Foreign Application Priority Data

Nov. 22, 2004 (IL) .......................................... 165334

(51) Int. Cl.
    *A61K 38/54* (2006.01)
(52) U.S. Cl.
    USPC ..... 424/94.2; 424/94.1; 424/94.65; 424/94.5; 424/94.63; 435/219
(58) Field of Classification Search
    USPC ................ 424/94.1, 94.2, 94.5, 94.63, 94.65; 435/219
    See application file for complete search history.

(56) References Cited

U.S. PATENT DOCUMENTS

| 4,197,291 | A | | 4/1980 | Klein | 424/94 |
| 4,226,854 | A | | 10/1980 | Klein | 424/94 |
| 4,286,064 | A | | 8/1981 | Galbraith | 435/219 |
| 4,307,081 | A | | 12/1981 | Klein | 424/94 |
| 4,320,120 | A | | 3/1982 | Mitsuhashi | 424/182 |
| 4,329,430 | A | | 5/1982 | Klein | 435/219 |
| 4,361,551 | A | | 11/1982 | Galbraith | 424/94 |
| 5,106,621 | A | | 4/1992 | Rowan | 424/94.65 |
| 5,387,517 | A | | 2/1995 | Cini | 435/212 |
| 5,505,943 | A | | 4/1996 | Fortney | 424/94.63 |
| 5,824,305 | A | * | 10/1998 | Mynott | 424/94.65 |
| 5,830,739 | A | * | 11/1998 | Houck et al. | 424/94.65 |
| 5,858,964 | A | | 1/1999 | Aharoni | 514/12 |
| 5,928,640 | A | * | 7/1999 | Mynott | 424/94.63 |
| 6,335,427 | B1 | | 1/2002 | Mynott | 530/379 |
| 6,803,038 | B1 | * | 10/2004 | Maurer et al. | 424/94.65 |
| 2002/0102253 | A1 | | 8/2002 | Mynott | 424/94.65 |
| 2002/0188107 | A1 | | 12/2002 | Mynott | 530/379 |
| 2003/0026794 | A1 | | 2/2003 | Fein | 424/94.1 |
| 2010/0272659 | A1 | | 10/2010 | Mueller et al. | 514/1.1 |

FOREIGN PATENT DOCUMENTS

| WO | WO 81/01242 A1 | 5/1981 |
| WO | WO 93/10811 A1 | 6/1993 |
| WO | WO 0014253 A1 * | 3/2000 |
| WO | WO 03/086275 A2 | 10/2003 |
| WO | WO 03/090598 A2 | 11/2003 |
| WO | WO 2008/021543 A2 | 2/2008 |

OTHER PUBLICATIONS

Davis, S.C. et al., (1990) Second-degree burn healing: The effect of occlusive dressings and a cream. *J Surg Res* 48(3):245-248.
Eldad, A. et al., (1998) Early nonsurgical removal of chemically injured tissue enhances wound healing in partial thickness burns. *Burns* 24(2):166-172.
Feinstein, Gad et al., (1964) On the Molecular Weights of the Proteolytic Enzymes of Stem Bromelain. *Biochemistry* 3(8):1050-1054.
Harrach, Tibor et al., (1995) Isolation and partial characterization of basic proteinases from stem bromelain. *J Protein Chem* 14(1):41-52.
Harrach, Tibor et al., (1998) Isolation and characterization of two forms of an acidic bromelain stem proteinase. *J Protein Chem* 17(4):351-361.
Houck, J.C. et al., (1983) Isolation of an effective debriding agent from the stems of pineapple plants. *Int J Tissue React* 5(2):125-134.
Ota, Shoshi et al., (1985) Reinvestigation of fractionation and some properties of the proteolytically active components of stem and fruit bromelains. *J Biochem (Tokyo)* 98(1):219-228.
Perlstein, Seymour H. et al., (1973) Isolation and characterization of a protease inhibitor from commercial stem bromelain acetone powder. *J Supramol Struct* 1(3):249-254.
Reddy, M.N. et al., (1975) Primary structural analysis of sulfhydryl protease inhibitors from pineapple stem. *J Biol Chem* 250(5):1741-1750.
Rosenberg, Lior et al., (2004) Safety and efficacy of a proteolytic enzyme for enzymatic burn débridement: a preliminary report. *Burns* 30(8):843-850.
Rowan, Andrew D. et al., (1988) Ananain: a novel cysteine proteinase found in pineapple stem. *Arch Biochem Biophys* 267(1):262-270.
Rowan, A.D. et al., (1990) The cysteine proteinases of the pineapple plant. *Biochem J* 266(3):869-875.
Vesterberg, Olof et al., (1966) Isoelectric fractionation, analysis, and characterization of ampholytes in natural pH gradients. IV. Further studies on the resolving power in connection with separation of myoglobins. *Acta Chem Scand* 20(3):820-834.

(Continued)

*Primary Examiner* — Susan Hanley
(74) *Attorney, Agent, or Firm* — Winston & Strawn LLP

(57) ABSTRACT

The present invention relates to a debriding composition obtained from bromelain and to methods of producing same. Particularly, the present invention relates to a debriding composition obtained from bromelain comprising proteolytic enzymes having molecular weights of about 23 kDa, being essentially devoid of bromelain inhibitors, and to pharmaceutical compositions comprising same. The debriding compositions and the pharmaceutical compositions comprising same are particularly useful in debriding eschar tissues and in wound healing.

5 Claims, 8 Drawing Sheets

(56) References Cited

OTHER PUBLICATIONS

Wharton, Christopher W. (1974) the structure and mechanism of stem bromelain. Evaluation of the homogeneity of purified stem bromelain, determination of the molecular weight and kinetic analysis of the bromelain-catalysed hydrolysis of N-benzyloxycarbonyl-L-phenylalanyl-L-serine methyl ester. *Biochem J* 143(3):575-586.

NCBI printout for Cysteine Proteinase Precursor CAA08861, retrieved from http://www.ncbi.nlm.nih.gov/protein/caa08861 on May 16, 2011.
"Plurality" Merriam-Webster.com 2010 retrieved from http://www.merriam-webster.com/dictionary/plurality on Dec. 8, 2010.
ISR of PCT/IL05/001236 mailed Jan. 16, 2008.
EP 5804486 Supplementary Search Report Dec. 17, 2010.

* cited by examiner

DEBRIDING COMPOSITION FROM BROMELAIN AND METHODS OF PRODUCTION THEREOF

CROSS-REFERENCE TO RELATED APPLICATIONS

This application is a continuation of application Ser. No. 11/719,586 filed May 17, 2007, now U.S. Pat. No. 8,119,124, which is the 371 US national phase of International application PCT/IL2005/001236 filed Nov. 22, 2005.

FIELD OF THE INVENTION

The present invention relates to a debriding composition obtained from bromelain and to methods of producing same. Particularly, the present invention relates to a debriding composition obtained from bromelain comprising proteolytic enzymes having molecular weights of about 23 kDa, being essentially devoid of bromelain inhibitors, and to pharmaceutical compositions comprising same. The debriding compositions and the pharmaceutical compositions comprising same are particularly useful in debriding eschar tissues and in wound healing.

BACKGROUND OF THE INVENTION

Considerable effort has been made to develop debridement preparations that are capable of removing devitalized tissue without surgery. Devitalized tissue is formed in all disease processes, which are associated with skin trauma, such as decubitus ulcers, pressure necroses, incisions and burns. Efficient debridement is essential since devitalized tissue is an excellent culture medium for opportunistic infections. Septicemia resulting from infections is the major cause of death for the majority of severely burned patients.

Use of proteolytic enzymes and chemical agents to effect early debridement of devitalized tissue has not led to satisfactory debridement. The chemical agents such as tannic acid, salicylic acid, and pyruvic acid, were found to cause further damage to already injured tissues.

Proteolytic enzymes including papain, pinguinain, trypsin, fibrinolysin, and streptokinase have been described as debriding agents. U.S. Pat. No. 5,505,943 discloses compositions containing a protease produced by microorganisms of the genus *Vibrio* for treating wounds by hydrolyzing components of necrotic tissue.

However, debridement by purified proteolytic enzymes suffers from various disadvantages as the purified enzymes require numerous applications over a long period of time, show poor efficacy, have toxic side effects and have no selectivity.

Extracts derived from the stem of the pineapple plant (*Ananas comosus*) have been found to selectively remove devitalized tissue. Such extracts, also named bromelain, contain various proteolytic and hydrolytic enzymes.

U.S. Pat. No. 4,197,291 discloses an enzyme product obtained from bromelain capable of debridement of devitalized tissue from a mammalian host, the enzyme product comprises a water soluble, heat labile protein that is free of caseinolytic activity and has a peak isoelectric point of about 6. The protein comprises at least two subunits, each of which having a molecular weight from about 14.3 to 15 kDa with a characteristic absorption peak in the ultraviolet region of the spectrum at 280 nm. The procedure to prepare such enzyme product as disclosed in U.S. Pat. No. 4,197,291 comprises protein precipitation with acetone, extraction of the precipitate with acetate buffer containing thioglycolic acid, filtration of the solution through a membrane with a molecular weight cut off of about 50 kDa, gel filtration of the filtrate, and isoelectric focusing. The enzyme product thus prepared contains at least two, most likely three, subunits having a molecular weight of 14.3 to 15 kDa. U.S. Pat. No. 4,226,854 discloses a method for debridement of devitalized tissue using the enzyme product disclosed in U.S. Pat. No. 4,197,291.

U.S. Pat. No. 4,329,430 further discloses a proteolytic enzyme mixture derived from bromelain useful for dissecting and digesting devitalized tissue. The proteolytic enzyme mixture which is heat labile and water soluble contains escharase, a hydrolytic enzyme free of caseinolytic activity with an isoelectric point of about 6, which comprises at least two subunits, each of which has a molecular weight from about 14.3 to 15 kDa. All of the components of the proteolytic enzyme mixture have a native molecular weight of from about 30 to 50 kDa as the enzyme mixture is filtered through a membrane having a molecular weight cut off of 50 kDa and concentrated over a membrane having a molecular weight cut off of 30 kDa. The reproducible results obtained with the proteolytic enzyme mixture are purportedly due to the fact that the enzyme mixture does not contain an inhibitor, which was apparently present in the previously published proteolytic enzyme preparations. However, there is no criterion for the detection of the activity of this inhibitor.

U.S. Pat. No. 4,307,081 discloses a method of dissecting and digesting devitalized tissue, which comprises contacting the tissue with the proteolytic enzyme mixture disclosed in U.S. Pat. No. 4,329,430.

The pineapple plant has been the source of various proteolytic enzymes. For example, U.S. Pat. No. 5,106,621 discloses purified cysteine proteinases derived from pineapple plant material having a molecular weight of about 25 kDa and exhibiting activity toward a coumarylamide substrate. Particularly, U.S. Pat. No. 5,106,621 relates to the cysteine proteinases ananain and comosain, which exhibit different physicochemical characteristics distinct from stem bromelain. A purified thiol activated protease having a molecular weight of about 17 kDa to 21 kDa, named α-Bromelain, is disclosed in U.S. Pat. No. 5,387,517, and is shown to have debridement activity. In addition, bromelain contains an acid phosphatase and a peroxidase and may contain amylase and cellulase activity. U.S. Pat. No. 6,335,427 teaches the purification of a 25 kDa protein from bromelain, the protein has been found to have anti-cancer activity.

Perlstein and Kezdy (J. Supramol. Struct. 1: 249-254, 1973) identified seven closely related protease inhibitors, i.e., bromelain inhibitor I-VII, from commercial bromelain acetone powder. The inhibitors were shown to have molecular weights of 5000-6000 Dalton and to contain 50 amino acid residues and five disulfide bonds (Perlstein and Kezdy, ibid). Primary structural analysis of one of the seven inhibitors revealed extensive microheterogeneity (Reddy, M. N. et al. J. Biol. Chem. 250: 1741-1750, 1975).

U.S. Pat. No. 5,830,739 discloses methods for preparing a stable admixture of escharase and other proteolytic enzymes from bromelain, which comprise extracting bromelain with a dilute ascorbic acid solution, followed by precipitating the escharase and other proteolytic enzymes with ammonium sulfate. U.S. Pat. No. 5,830,739 further teaches that the ammonium sulfate precipitate can be washed with distilled water over a 10 kDa ultrafilter. The method for preparing the stable admixture of escharase is found to yield higher amounts of escharase. However, there is no indication that the admixture is devoid of bromelain inhibitors.

Purified distinct enzymes isolated from bromelain were found to be not as efficient in debridement of non-viable tissues as a proteolytic enzyme mixture obtained from bromelain. However, proteolytic enzyme mixture obtained from bromelain, which contains proteins of molecular weights of up to 50 kDa including bromelain inhibitors was found to be not as effective in debridement of non-viable tissues as an enzyme mixture obtained from bromelain containing proteins of molecular weights of 30 to 50 kDa, which presumably was devoid of the inhibitors.

Since such enzyme mixtures are intended for human clinical use, there is an unmet need to obtain a biochemically characterized enzyme mixture from bromelain, which has distinct and reproducible biochemical features, essentially devoid of bromelain inhibitors and containing most of the proteolytic enzymes of bromelain, so that efficient debridement of non-viable tissues is obtained.

SUMMARY OF THE INVENTION

The present invention provides a debriding composition obtained from bromelain capable of debridement of non-viable tissues and having distinct biochemical features. Particularly, the present invention provides a debriding composition obtained from bromelain, biochemically characterized as being essentially devoid of bromelain inhibitors while comprising most of the proteolytic enzymes of bromelain. The enzyme composition thus obtained is highly efficient in debridement of non-viable tissues.

It is now disclosed, for the first time, that an enzyme composition obtained from bromelain having most of the proteolytic enzymes of bromelain, but essentially devoid of bromelain inhibitors, has superior debridement activity over that of bromelain. It is disclosed herein below that while bromelain contains at least three major protein peaks having molecular weights of about 6, 17.5 and 23 kDa when eluted from an HPLC size exclusion column, the enzyme composition of the present invention comprises predominantly one protein peak having molecular weights of about 23 kDa when applied to the same HPLC size exclusion column. The enzyme composition is highly reproducible in protein content and is thus advantageous for clinical use.

The method for preparing the enzyme composition according to the present invention comprises the steps of extracting commercially available bromelain powder with an acidic solution optionally comprising an anti-oxidant, adding a filter aid, filtering the suspension in order to remove insoluble components, precipitating the proteolytic enzymes by adding ammonium sulfate salt to the solution, dissolving the ammonium sulfate precipitate with an acidic solution optionally comprising an anti-oxidant, and filtering the solution, so that proteolytic enzymes having molecular weights in excess of about 10 kDa are retained.

According to one aspect, the present invention provides a debriding composition obtained from bromelain, the debriding composition comprising proteolytic enzymes having molecular weights of about 23 kDa, said composition being substantially devoid of bromelain inhibitors. The term "substantially devoid" refers to compositions comprising at most residual amounts of bromelain inhibitors compared to the amount present in crude bromelain extracts.

According to some embodiments, the bromelain inhibitors are less than 10% w/w of protein content of the debriding composition. Preferably, the bromelain inhibitors are less than 5% w/w of protein content of the debriding composition, more preferably the bromelain inhibitors are less than 2% w/w of protein content of the debriding composition, and most preferably the bromelain inhibitors are less than 1% w/w of protein content of the debriding composition.

According to a further embodiment, the debriding composition consists essentially of a single protein peak after elution from an HPLC size exclusion column TSK-Gel $3000_{SWXL}$, the single protein peak constituting proteins having molecular weights of about 23 kDa.

According to yet further embodiments, the single protein peak is obtained in a yield of at least 50% w/w of protein content of the debriding composition applied to the HPLC size exclusion column. According to another embodiment, the major protein peak is obtained in a yield of at least 60% w/w of protein content of the debriding composition. According to further embodiment, the major protein peak is obtained in a yield of at least 70% w/w of protein content of the debriding composition applied to the column.

According to additional embodiments, the debriding composition obtained from bromelain according to the principles of the present invention further comprises a pharmaceutically acceptable carrier.

According to another aspect, the present invention provides a method for obtaining a debriding composition from bromelain, the debriding composition comprising proteolytic enzymes having molecular weights of about 23 kDa, said composition being substantially devoid of bromelain inhibitors, the method comprising the following steps:

(a) suspending bromelain with an acidic solution optionally comprising an anti-oxidant, the acidic solution having a pH in the range from about 2.4 to about 4;
(b) adjusting the suspension of (a) to a pH in the range from about 2.4 to about 4;
(c) adding a filter aid to the suspension of (b);
(d) filtering the suspension of (c) to remove insoluble components;
(e) adding to the filtered solution of (d) ammonium sulfate salt to yield saturation of ammonium sulfate in the range from about 40% to about 50%;
(f) adjusting the suspension of (e) to a pH from about 2.5 to about 4;
(g) incubating the suspension of (f) at 3° C.-10° C.;
(h) centrifuging the suspension of (g) to yield an ammonium sulfate precipitate;
(i) dissolving the ammonium sulfate precipitate in an acidic solution optionally comprising an anti-oxidant having a pH in the range from about 2.4 to about 4;
(j) filtering the solution of (i) so that proteolytic enzymes having molecular weights in excess of about 10 kDa are retained; and
(k) lyophilizing the retained solution of (j).

According to a currently preferred embodiment, the present invention provides a method for obtaining a debriding composition from bromelain, the debriding composition comprising proteolytic enzymes having molecular weights of about 23 kDa, said composition being substantially devoid of bromelain inhibitors, the method comprising the following steps:

(a) suspending bromelain with 0.3 M acetic acid comprising 1% ascorbic acid and n-octanol having a pH from about 2.4 to about 2.6;
(b) adjusting the suspension of (a) to a pH in the range from about 2.5 to about 3.5;
(c) adding a filter aid comprising silica to the suspension of (b);
(d) filtering the suspension of (c) through a filter press to remove insoluble components;

(e) adding to the filtered solution of (d) ammonium sulfate salt (285 g/L) to yield 40% saturation of ammonium sulfate;

(f) adjusting the suspension of (e) to a pH from about 2.5 to about 3.5;

(g) incubating the suspension of (f) for approximately 12-24 hours at 4° C.;

(h) centrifuging the suspension of (g) to yield an ammonium sulfate precipitate;

(i) dissolving the ammonium sulfate precipitate in 0.3 M acetic acid comprising 1% ascorbic acid having a pH from about 2.4 to about 2.6;

(j) filtering the solution of (i) through a 10 kDa ultra-filter, so that proteolytic enzymes having molecular weights in excess of about 10 kDa are retained;

(k) filtering the retained solution of (j) to yield a sterile solution; and (l) lyophilizing the filtered solution of (k).

According to a further aspect, the present invention provides a method of treating a wound by debriding non-viable tissues comprising applying thereto a debriding composition according to the principles of the present invention.

According to some embodiments, a wide variety of wounds can be treated with the pharmaceutical composition of the invention including, but not limited to, full and partial thickness burn wounds, sunburns, frostbite; ulcerative lesions such as pressure (decubitus) ulcers and varicose, stasis and trophic ulcers; wounds associated with surgical procedures such as amputation, incision, circumcision and episiotomy; traumatic and pyogenic wounds; vaginitis; cervicitis; pilonidal cyst wounds; and cataract scar tissue. The pharmaceutical compositions of the invention are also useful for the preparation of skin graft sites.

These and other embodiments of the present invention will be better understood in relation to the figures, description, examples, and claims that follow.

DETAILED DESCRIPTION OF THE INVENTION

Figure 1:
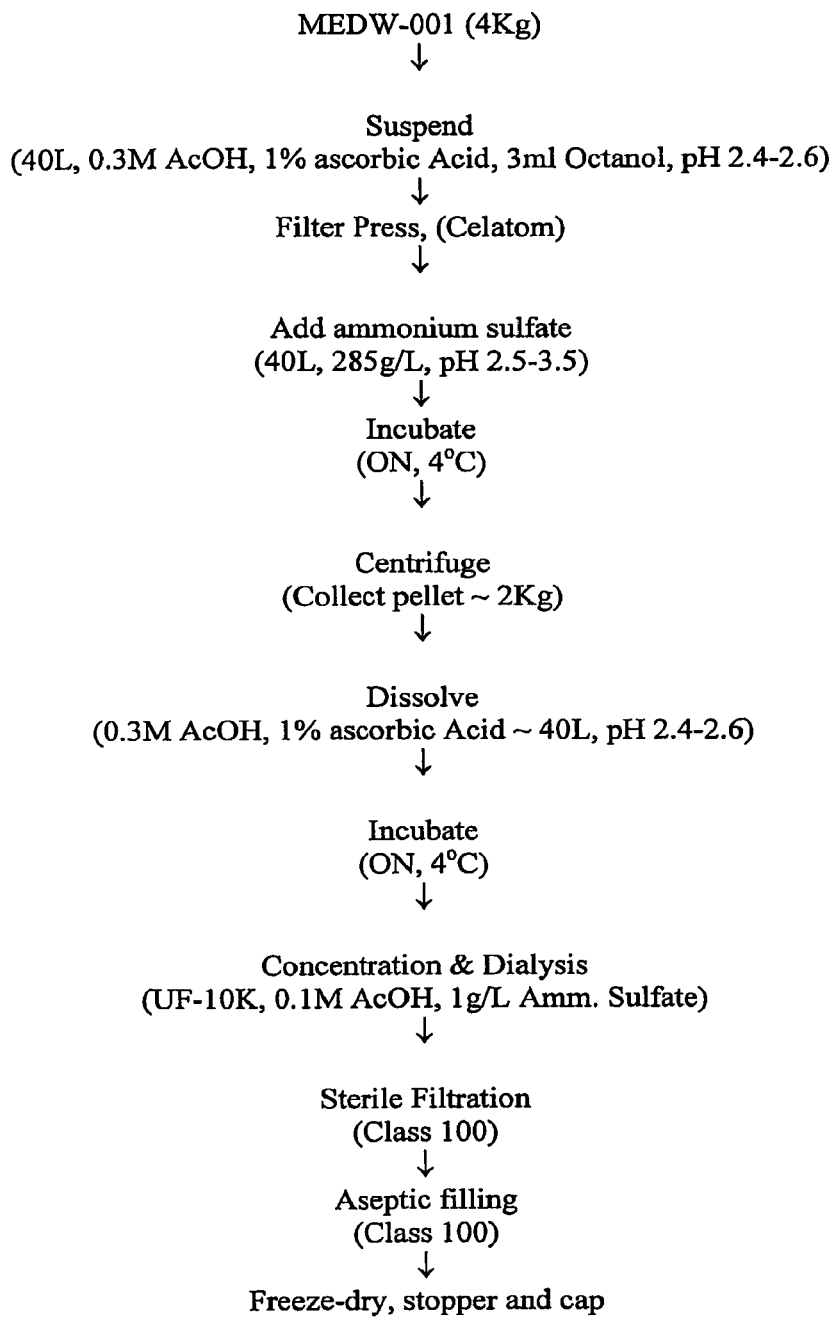
FIG. 1 shows a scheme of the method for preparing Debrase from bromelain.

The present invention provides a debriding composition obtained from bromelain, the composition comprising proteolytic enzymes having molecular weights of about 23 kDa, being substantially devoid of bromelain inhibitors. The invention further provides methods for obtaining said debriding composition and methods of using thereof.

It is now disclosed, for the first time, that combining two new steps, i.e., addition of filter aid and filtration, to the method for preparing a proteolytic mixture from bromelain as disclosed in U.S. Pat. No. 5,830,739, enables obtaining a debriding composition having improved biochemical and biological features. The debriding composition of the present invention contains most of the proteolytic enzymes of bromelain, i.e., enzymes having molecular weights in excess of about 10 kDa, but is essentially devoid of low molecular weight proteins, i.e., bromelain inhibitors having molecular weights of about 5-6 kDa. The composition has superior debridement activity over that of bromelain and shows reproducible protein content.

According to one aspect, the present invention provides a debriding composition obtained from bromelain, the debriding composition comprising proteolytic enzymes having molecular weights of about 23 kDa, wherein said composition is substantially devoid of bromelain inhibitors.

As used throughout the specification and claims, the term "bromelain" refers to any of a number of presently commercially available bromelain powder preparations. Examples of manufacturers of bromelain include, but are not limited to, Sigma and Challenge Bioproducts Co. Ltd., Taiwan. Bromelain is prepared from the stem of pineapple plant. A typical procedure to obtain bromelain is as follows: the juice from the stem of pineapple plant is first adjusted to a pH of about 3 or 4 with phosphoric acid, and sodium hydride or sodium sulfhydride is added to protect against sulfhydryl oxidation. The inert material is precipitated at about 30% acetone and, after filtration, the clarified fluid is precipitated with 70% acetone. This precipitate is collected by centrifugation and either redissolved in water containing sodium hydride or sodium sulfhydride which has been acidified with phosphoric acid and reprecipitated, or dried in a vacuum oven directly. If the material is reprecipitated, 70% acetone is utilized. The dried material from either process is suitable as a starting material to obtain the debriding composition of the present invention.

A previously published method for obtaining proteolytic mixture from bromelain, which method comprising a step of concentrating the solution over 30 kDa cut-off membranes, was suggested to eliminate bromelain inhibitors (see U.S. Pat. No. 4,329,430). However, as the method disclosed in U.S. Pat. No. 4,329,430 comprises the step of concentrating the solution over 30 kDa cut-off membranes, other proteins having molecular weights of up to 30 kDa were presumably removed by the concentration as well. Another previously published method comprises a step of filtering the extract through 10 kDa cut-off membranes (see U.S. Pat. No. 5,830,739), however no indication for the absence of bromelain inhibitor activity was provided. In contrast to the prior art, the present invention provides means to further purify a debriding composition from bromelain and to biochemically characterize the debriding composition. As such, the debriding composition obtained according to the principles of the present invention is shown to be substantially devoid of bromelain inhibitors and is more active in debridement of non-viable tissues than previously published methods.

Bromelain inhibitors are polypeptides having molecular weights of approximately 5-6 kDa (see, for example, Perlstein, S. H. and Kezdy, F. J., Supramol. Struct. 1: 249-254, 1973). According to the Examples disclosed herein below, the debriding composition obtained from bromelain according to the principles of the present invention, comprises proteins having apparent molecular weights in excess of about 10 kDa, which composition being essentially devoid of bromelain inhibitors. The term "about" when refers to a molecular weight of a protein is meant to include 2 kDa above or below the molecular weight of the protein. For example, if a protein has a molecular weight of about 10 kDa, it is meant that the molecular weight of the protein can range from 8 kDa to 12 kDa.

The term "substantially devoid" refers to compositions comprising at most residual amounts of bromelain inhibitors compared to the amount present in crude bromelain extract, i.e., the starting material from which the debriding composition of the invention is obtained. The term "residual amount" as used herein is meant to indicate that the bromelain inhibitors constitute not more than 10% w/w of protein content of the debriding composition. Preferably, the bromelain inhibitors constitute not more that 5% w/w of the protein content of the debriding composition, more preferably not more that 2% w/w of the protein content of the debriding composition, and most preferably not more than 1% w/w of protein content of the debriding composition.

According to another aspect, the present invention provides a method for obtaining a debriding composition from bromelain, the composition comprising proteolytic enzymes having molecular weights of about 23 kDa, said composition being substantially devoid of bromelain inhibitors, the method comprising the following steps:

(a) suspending bromelain with an acidic solution having a pH in the range from about 2.4 to about 4;
(b) adjusting the suspension of (a) to a pH in the range from about 2.4 to about 4;
(c) adding a filter aid to the suspension of (b);
(d) filtering the suspension of (c) to remove insoluble components;
(e) adding to the filtered solution of (d) ammonium sulfate salt to yield saturation of ammonium sulfate in the range from about 40% to about 50%;
(f) adjusting the suspension of (e) to a pH from about 2.5 to about 4;
(g) incubating the suspension of (f) at 3° C.-10° C.;
(h) centrifuging the suspension of (g) to yield an ammonium sulfate precipitate;
(i) dissolving the ammonium sulfate precipitate in an acidic solution optionally comprising an anti-oxidant having a pH in the range from about 2.4 to about 4;
(j) filtering the solution of (i) so that proteolytic enzymes having molecular weights in excess of about 10 kDa are retained; and
(k) lyophilizing the retained solution of (j).

According to the invention, suspending bromelain is performed in any acidic solution having a pH between about 2.4 to 4. Examples of acidic solutions or buffers that can be used according to the present invention include, but are not limited to, acetic acid in water, acetate buffer and acetate buffer containing 1% thioglycolic acid, pH 2.4-4. According to certain exemplary embodiments, the acidic solution is selected from the buffers and solutions disclosed in U.S. Pat. Nos. 5,830,739 and 4,197,291, the content of which is incorporated by reference as if fully set forth herein.

The acidic solution can optionally comprise an anti-oxidant. Examples of anti-oxidants include, but are not limited to, ascorbic acid, dihydroquinon, butylated hydroxytoluene and dithiothreitol. The anti-oxidant can be added at a concentration of about 0.5% to about 2%, preferably at 1%.

The acidic solution can further comprise a wetting agent. Examples of wetting agents include, but are not limited to, n-octanol.

The pH of the acidic solution, which optionally comprises an anti-oxidant, should be in the range from about 2.4 to about 4. According to a certain preferred embodiment, the pH of the acidic solution, which optionally comprises an anti-oxidant, ranges from about 2.4 to about 2.6. The term "about" when refers to a pH of a solution or suspension is meant to indicate that 0.1 pH units above or below the indicated pH are within the scope of the present invention.

According to the invention, a filter aid is added to the suspension of (a). According to one embodiment, the filter aid comprises silica. Preferably, the filter aid is natural diatomite that is calcined so that faster flow rates are achieved.

Precipitating the desired proteins is performed by adding to the filtered solution of step (d) ammonium sulfate salt. Ammonium sulfate salt can be added to yield saturation of the ammonium sulfate at a range of between about 40% to about 50%. Preferably, ammonium sulfate salt can be added to yield 40% saturation of ammonium sulfate.

The suspension of step (f) is then incubated at a temperature between 3° C. to 10° C. Preferably, the suspension of step (f) is incubated for at least 10 hours at temperatures between 3° C. to 10° C. More preferably, the suspension of step (f) is incubated for 12-24 hours at 4° C.

At the end of the incubation, the suspension of step (g) is centrifuged to precipitate the desired proteins, i.e., the proteolytic enzymes. The precipitate is then dissolved in acidic solution optionally comprising an anti-oxidant. According to an exemplary embodiment, the suspension is incubated for at least 10 hours at 4° C.

The solution of step (i) is subjected to a step of filtering to retain proteolytic enzymes having molecular weights in excess of about 10 kDa. According to a preferred embodiment, the solution of step (i) is filtered through a membrane filter having a molecular weight cut off of about 10 kDa. It is to be understood that any filter membrane which is capable of removing bromelain inhibitors and other contaminants while retaining proteolytic enzymes having molecular weights in excess of 10 kDa is encompasses in the present invention.

The debriding composition can be lyophilized after filtration, can be washed with distilled water and then lyophilized or can be filtered and then lyophilized. According to a currently preferred embodiment, the debriding composition is filtered through a filter membrane having a pore size of at least about 0.5 μm to obtain a sterile solution, which is then lyophilized and stored. Typically, the debriding composition is stored dry, as it is less stable in the presence of moisture. The debriding composition is dissolved only prior to use.

According to a currently preferred embodiment, the method for obtaining the debriding composition from bromelain comprises the following steps:
(a) suspending bromelain with 0.3 M acetic acid comprising 1% ascorbic acid and n-octanol having a pH from about 2.4 to about 2.6;
(b) adjusting the suspension of (a) to yield a pH in the range from about 2.5 to about 3.5;
(c) adding a filter aid comprising silica to the suspension of (b);
(d) filtering the suspension of (c) through a filter press to remove insoluble components;
(e) adding to the filtered solution of (d) ammonium sulfate salt (285 g/L) to yield 40% saturation of ammonium sulfate;
(f) adjusting the suspension of (e) to a pH from about 2.5 to about 3.5;
(g) incubating the suspension of (f) for approximately 12-24 hours at 4° C.;
(h) centrifuging the suspension of (g) to yield an ammonium sulfate precipitate;
(i) dissolving the ammonium sulfate precipitate in 0.3 M acetic acid comprising 1% ascorbic acid having a pH from about 2.4 to about 2.6;
(j) filtering the solution of (i) through a 10 kDa ultra-filter, so that proteolytic enzymes having molecular weights in excess of about 10 kDa are retained;
(k) filtering the retained solution of (j) to yield a sterile solution; and
(l) lyophilizing the filtered solution of (k).

Pharmaceutical Composition

The present invention provides a debriding composition obtained from bromelain, which composition comprising proteolytic enzymes having molecular weights in excess of about 10 kDa, wherein said composition is essentially devoid of bromelain inhibitors.

According to some embodiments, the debriding composition of the present invention can further comprise a pharmaceutically acceptable carrier to yield a pharmaceutical composition.

The term "pharmaceutically acceptable carrier" refers to a vehicle which delivers the active components to the intended target and which does not cause harm to humans or other recipient organisms. As used herein, "pharmaceutical" will be understood to encompass both human and animal pharmaceuticals. Useful carriers include, for example, water, acetone, ethanol, ethylene glycol, propylene glycol, butane-1, 3-diol, isopropyl myristate, isopropyl palmitate, or mineral oil. Methodology and components for formulation of pharmaceutical compositions are well known, and can be found, for example, in Remington's Pharmaceutical Sciences, Eighteenth Edition, A. R. Gennaro, Ed., Mack Publishing Co. Easton Pa., 1990.

The pharmaceutical composition can be formulated in any form appropriate for application to patients. The generally preferred route of administration is by topical application to the site to be treated. Accordingly, the pharmaceutical composition can be formulated in a form suitable for topical application, for example, in solutions, suspensions, creams, lotions, gels, foams, sprays, dry powder, and the like. The pharmaceutical composition can be applied directly to the injured tissue or can be applied to an inert dressing, such as gauze pad, and then applied to the injured tissue.

The pharmaceutical compositions can also comprise other optional materials, which can be chosen depending on the carrier. Additional components include, but are not limited to, preservatives such as Thimerosal, benzyl alcohol or parabens, thickening agents such as polyethylene glycol, hyaluronic acid, carbapol or glycerol, antimicrobial agents such as antibiotics or antifungal agents, and bulking substances such as lactose or mannitol. A keratinolytic agent such as urea may be added to aid in dissecting the eschar tissue.

Therapeutic Use of the Debriding Composition

The present invention provides a method for debriding non-viable tissues comprising applying thereto a therapeutically effective amount of the debriding composition according to the principles of the invention.

According to one embodiment, the method for debriding non-viable tissues comprises applying a therapeutically effective amount of the debriding composition, wherein the debriding composition further comprises a pharmaceutically acceptable carrier.

The debriding composition of the invention is useful in treating wounds. Particularly, the debriding composition is useful in wound debriding and wound healing applications. The properties can be demonstrated in a number of test situations, including animal and human clinical trials. The most widely used assay is a partial thickness burn wound on pigs described by Mertz et al. (Journal Surgical Research (1990) 48:245-248).

For wound debridement, effectiveness is determined, among other indications, by absence, softening or dissolving of eschar; non-hydrolysis of viable tissue components; and/or non-irritation of the wound. For topical wound healing, effectiveness is determined, among other indications, by wound contracture, increased rate of healing and/or improved healing (i.e., maintain response to tactile stimulus, less scarring, improved neovascularization, etc.). Thus, the term "therapeutically effective amount" refers to the amount of the debriding composition required to eliminate or reduce the eschar tissue and/or to promote wound healing.

A wide variety of wounds can be treated with the pharmaceutical composition of the invention including, but not limited to, full and partial thickness burn wounds; ulcerative lesions, principally pressure (decubitus) ulcers and varicose, stasis and trophic ulcers; surgical wounds such as amputation, incisional, traumatic and pyogenic wounds; treatment of vaginitis, cervicitis, circumcisions, episiotomy, pilonidal cyst wounds, carbuncles, sunburn, frostbite, and cataract scar tissue.

Debriding of non-viable tissues by the debriding compositions or the pharmaceutical compositions of the invention can be performed by single application on the eschar tissue or by several applications so long as the debridement is achieved. The method of debriding of the eschar tissue according to the present invention can be performed in combination with other known debriding methods.

The following examples are presented to provide a more complete understanding of the invention. The specific techniques, conditions, materials, proportions and reported data set forth to illustrate the principles of the invention are exemplary and should not be construed as limiting the scope of the invention.

Example 1

Preparation of Debrase

Suspension of Bromelain

Bromelain SP (4 Kg powder; Challenge Bioproducts Co. Ltd., Taiwan) was suspended in 40 liters of a suspension solution containing 0.3M acetic acid, 1% ascorbic acid, and 70 mg/ml n-octanol, pH 2.4-2.6 and conductivity 1.0-1.2 mS as follows: the suspension solution was freshly prepared (not more than one day prior to use) and was pre-cooled to 3-5° C. Bromelain was slowly added to the pre-cooled suspension solution under stirring. After 10 min the pH of the suspension was measured and adjusted to 2.5-3.5 with 1M acetic acid or 0.1M sodium hydroxide. The suspension was continuously stirred at 3-5° C., overnight (FIG. 1).

Filtration Through Filter Press

After overnight incubation, the suspension was diluted with an equal volume of a dilution solution containing 0.3M acetic acid and 1% ascorbic acid (pH 2.4-2.6). A filter aid, Celite Hyflo (60 g/L; Merck, Germany), was slowly added to the diluted suspension with continuous stirring for at least 15 min. The suspension was then filtered through a Filter Press (Celatom, Difenbach, Italy) equipped with filtering pads IF 350 and CRESPASTE 110 (Indastrialfiltro, Italy) to remove insoluble components. After the first round of the filtration, the protein solution (filtrate) was re-circulated through the Filter Press, and the clear filtrate was collected and pre-cooled to 3-5° C. At the end of the filtration, the filter press was rinsed with about 20 L of the dilution solution and purged with air to remove residual proteins from the filter. The solution containing the residual proteins from the filter was combined with the filtrate and stirred continuously at 4-6° C.

Precipitation with Ammonium Sulfate

Ammonium sulfate (285 g/L) was added slowly to the stirred filtrate. The pH of the resulting solution was adjusted to 2.5-3.5 with 1M acetic acid or 0.1M sodium hydroxide. After 10-15 min, the stirring was stopped and the solution was incubated overnight at 3-5° C.

Centrifugation

The protein solution containing ammonium sulfate was separated by centrifugation at 14,000 g. The supernatant was discarded and the precipitate was collected.

Protein Dissolution

The precipitate was re-suspended overnight at 3-5° C. in 40 L of a freshly prepared dilution solution containing 0.3M acetic acid and 1% ascorbic acid, pH 2.4-2.6 under stirring as follows: the dilution solution was prepared and pre-cooled to 3-5° C. The precipitate was added slowly to the dilution solution for about 15 min with continuous stirring. The suspension was stirred at 3-5° C. overnight.

Ultra Filtration (Concentration and Dialysis)

The suspension was pre-filtered through a 0.5 µm Milligard filter (Millipore, France). The filtrate was collected. At the end of the filtration, the filter was purged with air to remove residual proteins. The filtered solution was then dia-filtered through an ultra filtration unit containing 4 membranes with 10 kD MW cut-off (Millipore; Pelicon-2; 10 KD). The assembled ultra-filtration system was pre-rinsed with distilled water and then equilibrated with a dialysis solution containing 0.1M acetic acid and 1 g/l ammonium sulfate. The protein solution was first concentrated to a protein concentration of about 100 g/l (about 10 liter) and dialyzed against 4.5-5 volumes of the dialysis buffer to reach conductivity of ≦3.8 mS and pH 3±0.2. The solution was stirred at ≦15° C. At the end of the dia-filtration, the volume of the retentate was reduced to about 5 L. The ultra filtration membranes were then rinsed with the dialysis solution up to a final volume of 10 L.

Sterile Filtration and Freeze-Drying

The dia-filtered solution was filtered through a 0.5 µm Milligard pre-filter and then through an absolute 0.22 µm Millidisk 40 filter (Millipore, France). The filtrate was collected into lyophilization stainless steel trays and lyophilized in a freeze-dryer (USIFROID, France). The lyophilized debriding composition thus prepared is named herein Debrase.

Filling

Filling of the lyophilized Debrase powder was performed according to a preset weight. Debrase was filled into pyrogen-free glass bottles (30 ml (Saint-Gobain, France) and closed with plastic caps. Filled bottles were stored in a freezer at −20° C. The amount of Debrase powder produced from 4 Kg bromelain was 720-750 g per batch.

Example 2

Debrase is Devoid of Bromelain Inhibitors

Purification of Bromelain Inhibitors

Bromelain powder (2.5 g) was suspended in 10 ml of 0.1M potassium phosphate buffer pH 6.1 saturated with phenyl mercury acetate for 10 min. After centrifugation for 10 min (3500 rpm), one ml of the supernatant was applied to gel filtration chromatography on a HiLoad 16/60 Superdex 75 HPLC preparation grade column, equilibrated and eluted with the same buffer. Fractions of 5 ml were collected 30 minutes after sample application. For each of the eluted fractions, three parameters were measured: (i) absorbance at 280 nm ($A_{280}$); (ii) esterolytic activity; and (iii) inhibition of Debrase esterolytic activity.

The esterolytic activity of the bromelain fractions was assayed spectrophotometrically at pH 4.6 using the chromogenic substrate p-nitrophenyl Na-benzyloxycarbonyl-L-lysinate (CLN) as follows:

One milliliter of sodium acetated buffer (10 mM) containing 0.1 M KCl and 1 mM L-cysteine, pH 4.6 was placed in a plastic cuvette at 25° C. One hundred µl of the eluted fraction (at a concentration of 2.5 mg/ml) were added. The solution was incubated for 2 min and then 50 µl of CLN solution (2.5 mM in acetonitrile 10% water) were added. The cuvette was mixed and the increase in absorbance at 317 nm was monitored for 5 minutes. The spontaneous hydrolysis of the substrate was monitored in the presence of buffer only instead of the eluted fractions.

The inhibition of the esterolytic activity of Debrase was measured as follows: Twenty µl of Debrase (0.25 mg/ml) were incubated with the various HPLC fractions and the esterolytic activity of Debrase was assayed spectrophotometrically at pH 4.6 using CLN as described above.

Figure 2:
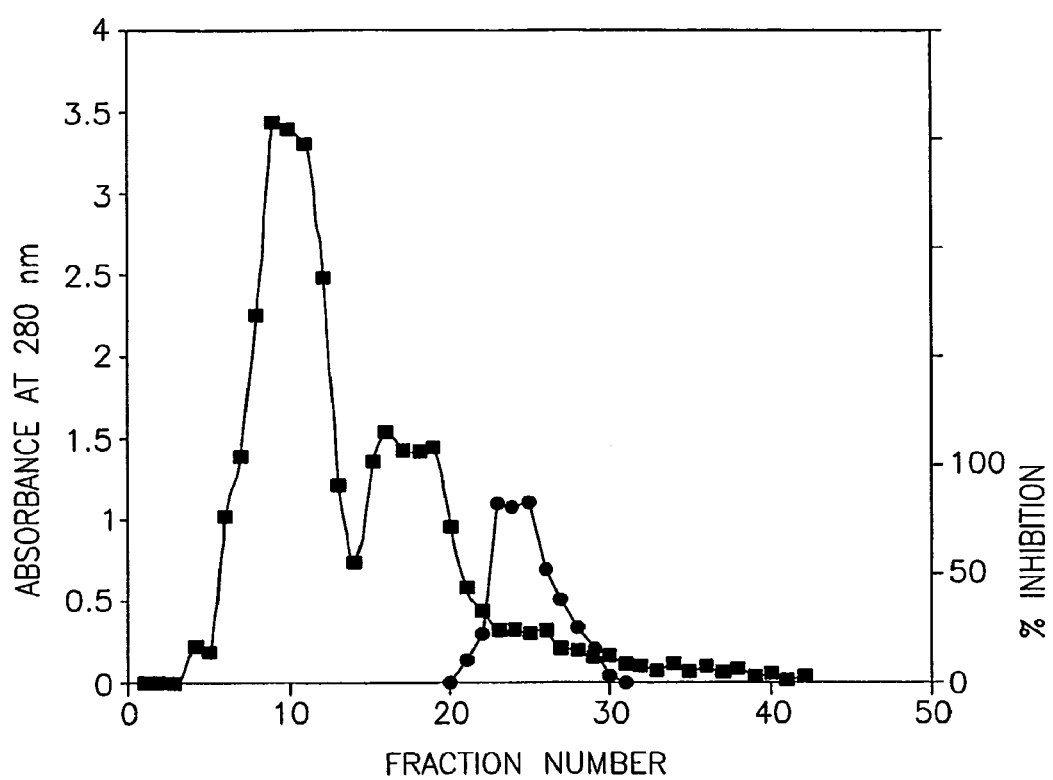
FIG. 2 shows a size exclusion chromatogram of a crude extract of bromelain. Bromelain powder was extracted with phosphate buffer pH 6.1 saturated with phenyl mercury acetate and centrifuged. The supernatant was applied to a preparative size exclusion HPLC column and eluted with the same buffer. Fractions were collected. Squares represent absorbance at 280 nm and circles represent % of inhibition of Debrase esterolytic activity.

As shown in FIG. 2, Stem Bromelain was eluted in fractions 5-13 and 14-20. However, bromelain inhibitors, which show inhibition of Debrase esterolytic activity, were eluted in fractions 22-29.

Table 1 shows the esterolytic activity of Debrase in the absence or presence of eluted fractions #20-30. As seen in Table 1, fractions 22-29 inhibited Debrase esterolytic activity. The most pronounced inhibition was obtained with fractions 23-25. The apparent molecular weight of the inhibitory activity was shown to be about 5-6 kDa, thus indicating that Bromelain inhibitors eluted in fractions 23-25.

TABLE 1

Results of the esterolytic activity of Debrase in the presence of bromelain fractions.

| Compound | Proteolytic activity | % Inhibition |
|---|---|---|
| Debrase | 945 | 0 |
| +1 mM Iodoacetamide | 593 | 37.0 |
| +Fraction 20 (5 µg) | 938 | 0.7 |
| +Fraction 21 (5 µg) | 860 | 9.0 |
| +Fraction 22 (5 µg) | 732 | 22.5 |
| +Fraction 23 (5 µg) | 172 | 81.7 |
| +Fraction 24 (5 µg) | 185 | 80.4 |
| +Fraction 25 (5 µg) | 164 | 82.6 |
| +Fraction 26 (5 µg) | 457 | 51.6 |
| +Fraction 27 (5 µg) | 587 | 37.8 |
| +Fraction 28 (5 µg) | 710 | 24.8 |
| +Fraction 29 (5 µg) | 802 | 15.1 |
| +Fraction 30 (5 µg) | 920 | 2.6 |

HPLC Analysis of Debrase

Size exclusion chromatography of Debrase and its starting material bromelain was performed in order to characterize and analyze the differences between these two enzymatic mixtures. Debrase and bromelain were each applied on a TSK gel $3000_{SWXl}$ HPLC column and the column was run at a flow rate of 0.4 ml/min of 40 mM phosphate buffer containing 130 mM NaCl.

Figure 3:
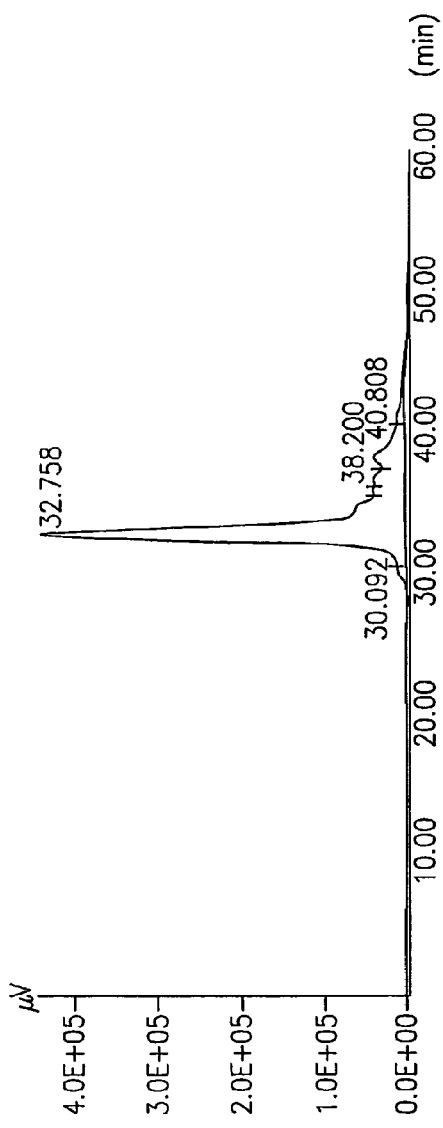
FIG. 3 shows size exclusion chromatograms of Debrase (upper panel) and bromelain (lower panel). Bromelain was subjected to size exclusion chromatography and three protein peaks (i.e., peaks numbered 1, 2 and 3) appeared at approximately 32, 35 and 40 min, respectively (lower panel). Debrase was subjected to the same size exclusion chromatography and only one protein peak appeared at approximately 32 min (upper panel). Peaks nos. 2 and 3, which appeared in the chromatogram of bromelain, were undetectable in the Debrase chromatogram. Peak no. 3 was identified as bromelain inhibitor, and peak no. 2 was considered either a contaminant or an inhibitor.
Figure 3:
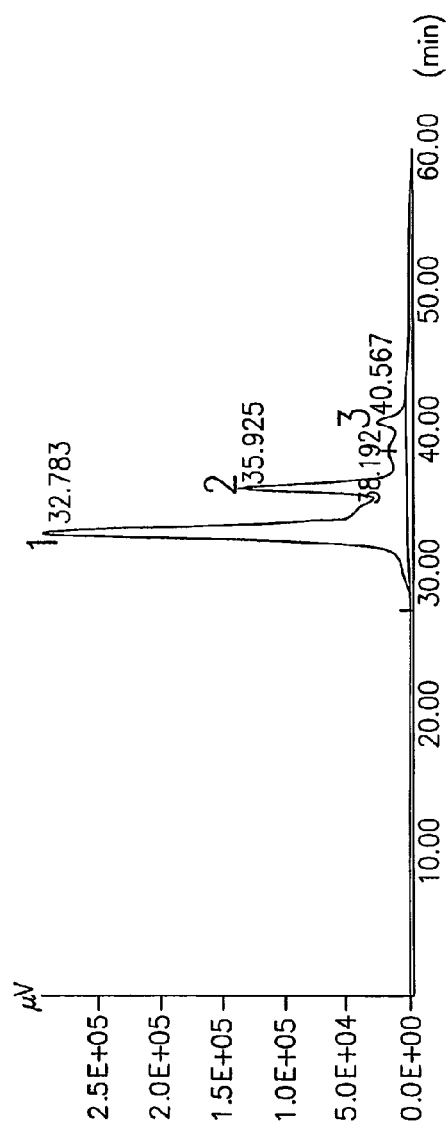

FIG. 3 shows that while in Debrase chromatography only one protein peak was obtained (upper panel), in bromelain chromatography three peaks were obtained (lower panel). Two of the main peaks in bromelain were identified: peak no. 1 was identified as Stem Bromelain while peak no. 3 was identified as bromelain inhibitor. As seen in FIG. 3, bromelain inhibitors were essentially absent from Debrase, thus indicating that the method for preparing Debrase enables removal of bromelain inhibitors, thereby producing inhibitor free enzyme composition.

SDS-polyacrylamide gel electrophoresis followed by mass spectrometry of the proteins present in Debrase and in a proteolytic mixture prepared according to U.S. Pat. No. 5,830,739, the content of which is incorporated by reference as if fully set forth herein, showed that the proteolytic mixture prepared according to U.S. Pat. No. 5,830,739 contained stem bromelain, stem bromelain precursor, ananain, and ananacо precursor as well as bromelain inhibitor 2 segment 2, while Debrase contained all of these enzymes and enzyme precursors, but was devoid of the bromelain inhibitor. These results, therefore, indicate that the method of preparing Debrase is highly efficient in eliminating bromelain inhibitors.

Example 3

Partial Identification of Proteins in Debrase

Debrase and a proteolytic mixture prepared according to U.S. Pat. No. 5,830,739 each was subjected to isoelectric focusing and SDS-PAGE as follows:

Samples of Debrase or of the proteolytic mixture were suspended in 200 µl of 5% trifluoric acid (TFA) in water for a few minutes at room temperature while mixing. The samples were then centrifuged at 20,000×g at 4° C. for 30 minutes and the supernatants were collected. Protein concentrations were determined by the method of Bradford. Samples of the supernatants containing 100 µg protein were lyophilized and resolubilized in a gel rehydration solution (8 M urea; 2 M thiourea; 5.2 µl/ml Pharmalites (pH 3-10); 10 mg/ml CHAPS (Sigma Chemicals Co.) and 2 mg/ml DTT) and were loaded on immobilized pH gradient (IPG) strips (18 cm, 3-10 linear pH gradient) for isoelectric focusing by incubation of the strips in the protein-containing rehydration solution for 24 hours. The isoelectric focusing was carried out in four steps: 1) 0-500 volt gradient for 1000 Volt hour (Vh); 2) a constant potential of 500 volts for 2500 Vh; 3) 500-3500 volt gradient for 10,000 Vh and 4) a constant potential of 3,500 volts for 35,000 Vh. Second dimension was SDS-PAGE gels of 12.5% acrylamide, 2.6% bisacrylamide. At the end of the SDS-PAGE, the gels were stained with colloidal Coomassie Blue.

Figure 7:
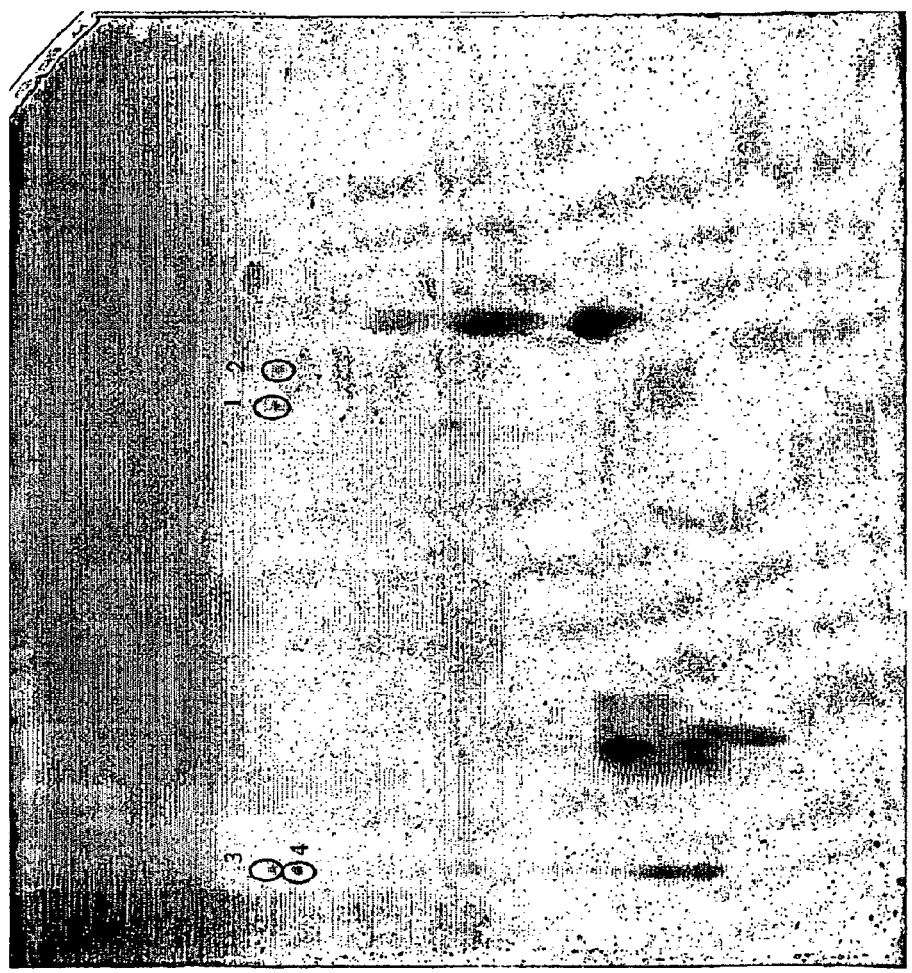
FIG. 7 shows a two-dimensional gel electrophoresis of Debrase obtained from bromelain. Debrase was isolated from bromelain (see Example 1 herein below) and subjected to two-dimensional gel electrophoresis. Four protein spots designated 1-4 were identified by MS/MS analysis.

FIG. 7 shows a Coomassie-blue stained SDS-PAGE of Debrase.

Figure 8:
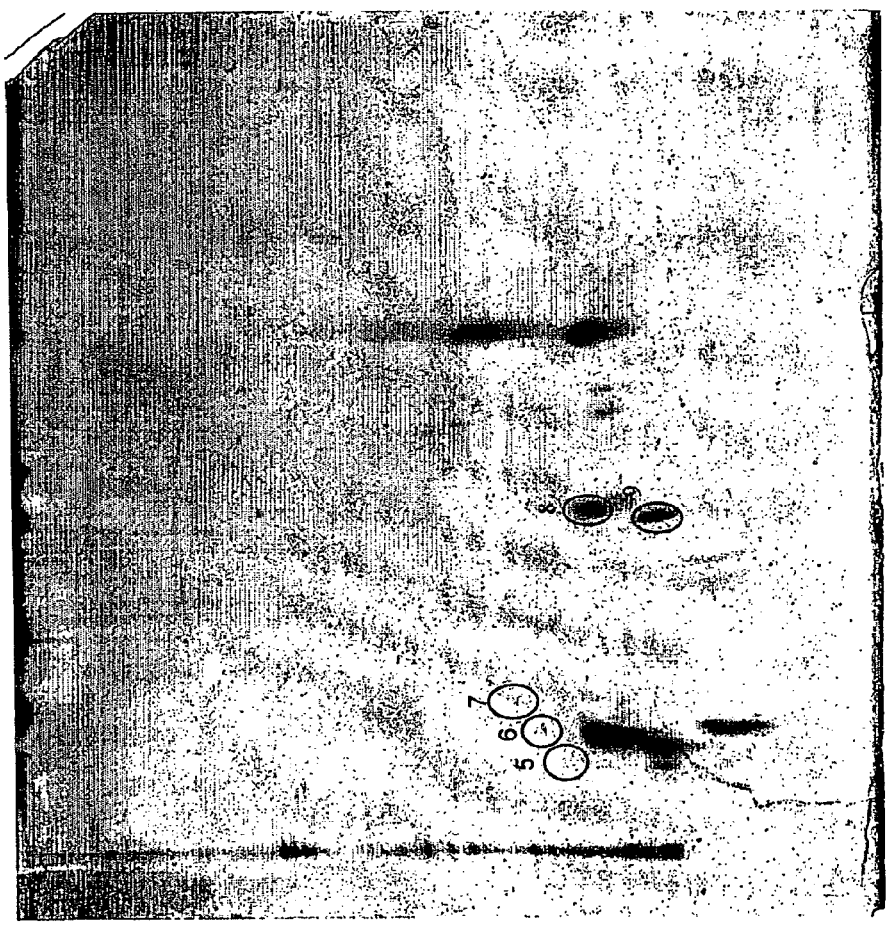
FIG. 8 shows a two-dimensional gel electrophoresis of a proteolytic mixture obtained from bromelain. A proteolytic mixture was prepared from bromelain according to the procedure described in U.S. Pat. No. 5,830,739. The mixture was subjected to two dimensional gel electrophoresis and five protein spots designated 5-9 were identified by MS/MS analysis.

FIG. 8 shows a Coomassie-blue stained SDS-PAGE of the proteolytic mixture prepared according to U.S. Pat. No. 5,830,739. As described herein above, Debrase and the proteolytic mixture were first subjected to electro focusing and then to SDS-PAGE.

Protein Identification

Spots were cut from each of the Coomassie-Blue stained SDS-PAGE gels and washed for 30 minutes in 200 µl of 200 mM $NH_4NCO_3$-50% $CH_3CN$ at 37° C. The washed spots were then dried, rehydrated with digestion solution (0.02 µml$^{-1}$ Trypsin (Promega); 40 mM $NH_4NCO_3$ (pH 8.1); 10% $CH_3CN$) and incubated for 16 hours at 37° C. Peptides were extracted by sonication in 10% $CH_3CN$ and the extracted peptides were loaded on a POROS 50 R2 (PerSeptive Biosystems) micro column for desalting. The peptides were eluted directly into a Q-STAR (Applied Biosystems) needle and were measured and analyzed using the Analyst QS software (Applied Biosystems). Sequences derived from the MS/MS analysis were used for short BLAST search in the NCBI database.

Table 5 lists the identity of the protein spots designated 1-4 and 5-9 in FIGS. 7 and 8, respectively.

TABLE 5

Proteolytic enzymes and bromelain inhibitors identified in Debrase or in the proteolytic mixture.

| Debrase | | The Proteolytic Mixture | |
|---|---|---|---|
| Spot number and Sequence | Protein | Spot number and Sequence | Protein |
| #1 AFEFIISNKG (SEQ ID NO: 1) | Stem bromelain EC 3.4.22.32 | #5 QDEYKCYC (SEQ ID NO: 5) | Bromelain inhibitor-pineapple XBPI |
| #2 IDWRDSGAVTS (SEQ ID NO: 2) | Ananain EC 3.4.22.31 | #6 CPGFCKTCKAE (SEQ ID NO. 6) | Bromelain inhibitor VI 566609 |

TABLE 5-continued

Proteolytic enzymes and bromelain inhibitors identified in Debrase or in the proteolytic mixture.

| Debrase | | The Proteolytic Mixture | |
|---|---|---|---|
| Spot number and Sequence | Protein | Spot number and Sequence | Protein |
| #3 YPYKAAKGTCKTDG (SEQ ID NO: 3) | Bromelain, stem P14518 | #7 CVCADTYSDC (SEQ ID NO: 7) | Bromelain inhibitor VII P01068_2 |
| #4 SRDEPSDPMMK (SEQ ID NO: 4) | Cysteine proteinase precursor CAA08861 | #8 ATVESIYKGEAGYIR (SEQ ID NO: 8) | FBSB precursor BAA22544 |
| | | #9 GSSWGEGGYVR (SEQ ID NO: 9) | Fruit Bromelain EC 3.4.22.33 |

As seen in Table 5, three types of Bromelain inhibitor (bromelain inhibitor—pineapple, bromelain inhibitor VI and VII) were identified in the proteolytic mixture, but not in Debrase. These results indicate that Debrase is essentially devoid of inhibitors.

Example 4

In-Vivo Activity of Debrase

The in-vivo pig burn wound model for the assessment of debriding efficacy of Debrase was used. Due to the close resemblance of young swine skin to that of humans, the in-vivo pig burn wound model is known to be an accepted model for cutaneous thermal burns in humans.

Burn-inflicting device consisting of a modified electric radiant heating element enclosed in a metal casing was adjusted to 400° C. for a period of 15 seconds to create deep burns on symmetrical dermatomes 3 cm along its central (spinal) line. The size of the burn was controlled by placing an asbestos template with a 4.5×4.5 cm square hole, held against the projected burn site on the pig's skin and the burn inflictor was attached to the hole at a standard distance from the skin. The adjacent skin was protected by the asbestos shields. An equal number of 5-14 pairs (depending of need) of deep burns were inflicted on each side. Once all burns were inflicted, the top keratin layer of the eschar was removed by wiping with normal saline-soaked Skleaner™ sponges until the clean exposed dermis was revealed. All the burn area were then hydrated by applying saline soaked gauze sponges to each burn for a period of approximately 1 hour, constantly reapplying saline to insure the burn areas did not dry out.

After about 1 hour of hydration, an adhesive barrier was placed around each burn area on the surrounding healthy skin. Five ml of a gel vehicle containing Carbomer 980 and dibasic sodium phosphate in water, pH 7.4, were then mixed with 0.5 gr of Debrase powder and applied over the wound extending to the inner edge of the adhesive barrier, covering an area of 5×5 cm. In control sites, only 5 ml of the gel were used. The entire wound, covered with the layer of the gel and surrounded by the adhesive barrier, was then covered with an occlusive film that adhered to the adhesive barrier. The occlusive film adhered intimately to the gel so that no air was trapped under the film. A small temperature probe was inserted through the adhesive barrier for monitoring the temperature of the gel in the chamber, which was kept at 37° C. to 40° C. by using a heating lamp. The entire back was covered with a soft cotton (gauze) dressing (Kerlix or the like) in order to stabilize all the occlusive dressings at the various sites. The dressing was left for four hours. Then, the dressing was removed, the gel with the dissolved eschar was wiped with a wooden tongue depressor and the wound bed scrubbed with the Skleaner until all loose or dissolved tissue was removed. After cleaning the wounds, the wounds were soaked with saline soaked gauze for another 1 hour and evaluated visually.

TABLE 2

In Vivo Activity of Bromelain and Debrase

| Debriding Substrate | Amount (g) | Carrier Used | Amount (g) | Final Score |
|---|---|---|---|---|
| Bromelain (batch 06 03) | 0.5 | Gel MG20/C05-08 | 0.5 | 2.5 |
| Bromelain (batch 06 03) | 0.5 | Gel MG20/C05-08 | 0.5 | 2 |
| Bromelain (batch 06 03) | 0.25 | Gel MG20/C05-08 | 0.5 | 2 |
| Bromelain (batch 06 03) | 0.25 | Gel MG20/C05-08 | 0.5 | 2 |
| Bromelain (batch 06 03) | 0.125 | Gel MG20/C05-08 | 0.5 | 1.5-2 |
| Bromelain (batch 06 03) | 0.125 | Gel MG20/C05-08 | 0.5 | 2 |
| Bromelain (batch 06 03) | 0.0625 | Gel MG20/C05-08 | 0.5 | 1-1.5 |
| Bromelain (batch 06 03) | 0.0625 | Gel MG20/C05-08 | 0.5 | 1.5 |
| Debrase MD2/D01-04 | 0.5 | Gel MG20/C05-08 | 0.5 | 5 |
| Debrase MD2/D01-04 | 0.5 | Gel MG20/C05-08 | 0.5 | 4.5 |
| Debrase MD2/D01-04 | 0.25 | Gel MG20/C05-08 | 0.5 | 4 |
| Debrase MD2/D01-04 | 0.25 | Gel MG20/C05-08 | 0.5 | 4 |
| Debrase MD2/D01-04 | 0.125 | Gel MG20/C05-08 | 0.5 | 3.5 |
| Debrase MD2/D01-04 | 0.125 | Gel MG20/C05-08 | 0.5 | 3.5-4 |

TABLE 2-continued

In Vivo Activity of Bromelain and Debrase

| Debriding Substrate | Amount (g) | Carrier Used | Amount (g) | Final Score |
|---|---|---|---|---|
| Debrase MD2/D01-04 | 0.0625 | Gel MG20/C05-08 | 0.5 | 3 |
| Debrase MD2/D01-04 | 0.0625 | Gel MG20/C05-08 | 0.5 | 3.5 |

As shown in Table 2, Debrase was found to be more efficient in debriding a burn wound than bromelain. For example, 0.5 g of Debrase yielded an average Visual Assessment Scoring (VAS) of 4.75 (the highest score is 5) compared to an average VAS of 2.25 for the same amount of bromelain. In addition, 0.25 g of Debrase debrided burn wound much better than bromelain (VAS 4 compared to VAS 2, respectively).

Example 5

Ex-Vivo Activity of Debrase

Ex-vivo assay based on digestion of pig skin tissue pieces by Debrase was performed. Pieces of pig ear skin (ca. 1 cm in diameter) were burned and subjected to Debrase proteolysis. The tear off time of the tissue by Debrase was monitored. The assay was performed as follows:

Pig ear skin was prepared by separating the skin from the cartilage and removing fat excess. Pig ear skin pieces were boiled for 20 sec and placed in the bottom of a skin holder with 5 ml PD-Tip above and the upper skin holder is tightened on top. Debrase or bromelain were mixed with an aqueous phase (e.g., Gel, Silverol or buffer) and applied into the bottom of the cell using either a syringe fitted with a plastic tube or a pipette. The tear off time of the skin ear pieces was measured.

Results

TABLE 3

Ex vivo debriding activity of Debrase.

| | MD5/C07-45 | | | | MD2/D01-45 | | | | |
|---|---|---|---|---|---|---|---|---|---|
| mg/ml | 1 | 2 | 3 | Avr. | 1 | 2 | 3 | Avr. | S.D |
| 0.375 | 181 | 272 | 272 | 241.7 | 265 | 270 | 236 | 257.0 | 18.36 |
| 0.75 | 263 | 200 | 237 | 233.3 | 216 | 261 | 144 | 207.0 | 59.02 |
| 1.56 | 193 | 101 | 163 | 152.3 | 132 | 131 | 168 | 143.7 | 21.08 |
| 3.125 | 127 | 128 | 131 | 128.7 | 118 | 103 | 87 | 102.7 | 15.50 |
| 6.25 | 74 | 61 | 30 | 55.0 | 56 | 78 | 68 | 67.3 | 11.02 |
| 12.5 | 62 | 57 | 60 | 59.7 | 48 | 65 | 48 | 53.7 | 9.81 |
| 25 | 43 | 16 | 33 | 30.7 | 44 | 42 | 49 | 45.0 | 3.61 |
| 50 | 88 | 21 | 55 | 54 | 33 | 52 | 22 | 35.67 | 15.18 |

TABLE 4

Exvivo debriding of activity of Bromelain

| | BSP 05 03 | | | | BSP 06 03 | | | |
|---|---|---|---|---|---|---|---|---|
| mg/ml | 1 | 2 | 3 | Avr. | 1 | 2 | 3 | Avr. |
| 0.375 | 232 | 232 | 231 | 231.7 | 231 | 230 | 229 | 230.0 |
| 0.75 | 144 | 240 | 136 | 173.3 | 240 | 240 | 171 | 217.0 |
| 1.56 | 149 | 180 | 141 | 156.7 | 240 | | 160 | 133.3 |
| 3.125 | 114 | 161 | 229 | 168.0 | 110 | 97 | 160 | 122.3 |
| 6.25 | 142 | 121 | 105 | 122.7 | 80 | 110 | 106 | 98.7 |
| 12.5 | 64 | 139 | 195 | 132.7 | 102 | 134 | 83 | 106.3 |
| 25 | 36 | 104 | 53 | 64.3 | 34 | 58 | 63 | 51.7 |
| 50 | 37 | 35 | 72 | 48.00 | 56 | 55 | 32 | 47.67 |

Figure 4:
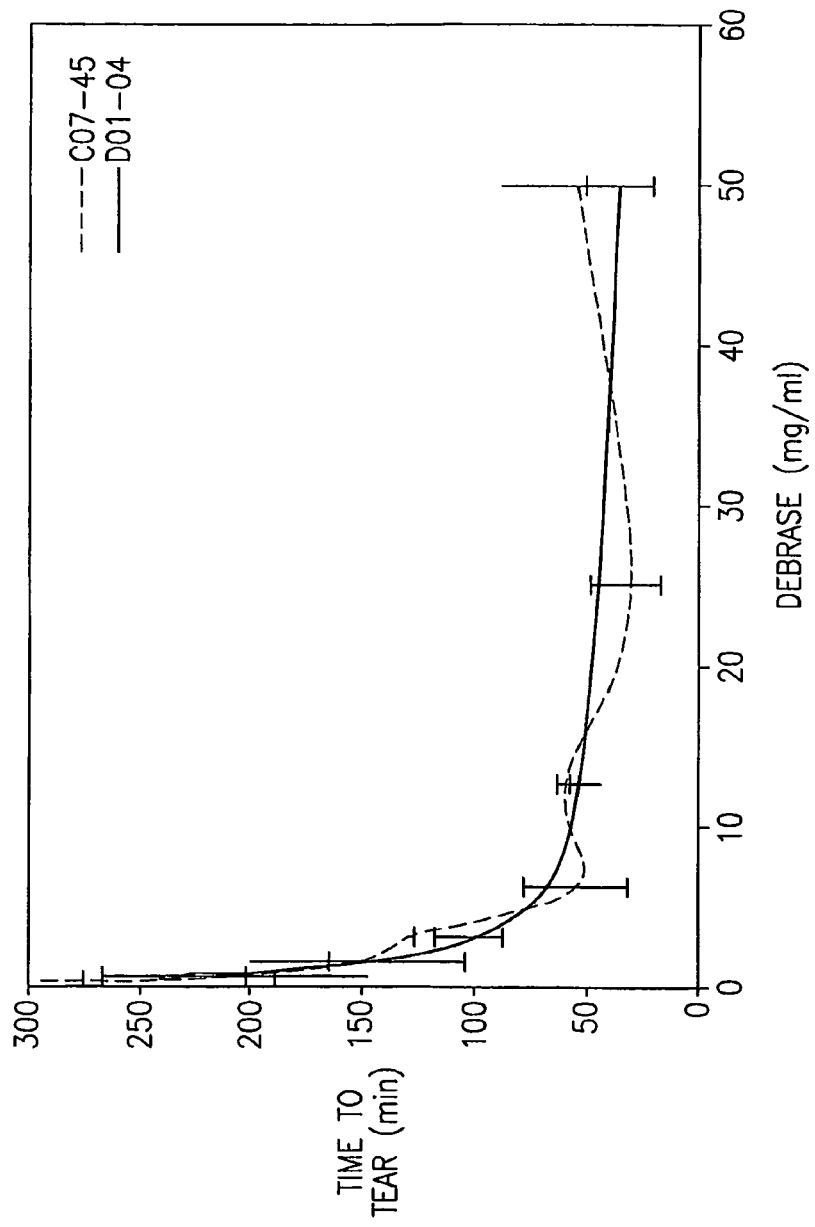
FIG. 4 shows the debriding activity of two preparations of Debrase on pig ear skin. The tear off time of pig ear skin pieces was measured as a function of Debrase concentrations.

Tables 3 and 4 show the ex-vivo activity difference between Debrase and bromelain. Table 3 and FIG. 4 show that Debrase at a concentration of 12.5 mg/ml in buffer debrided burned pig ear skin within 56.7±9.81 min. Higher concentrations of Debrase did not result in faster debridement. Lower concentrations of Debrase caused debridement at longer periods of time. The limit of detection for Debrase was 3.125 mg/ml (115.35±15.5 min).

Figure 5:
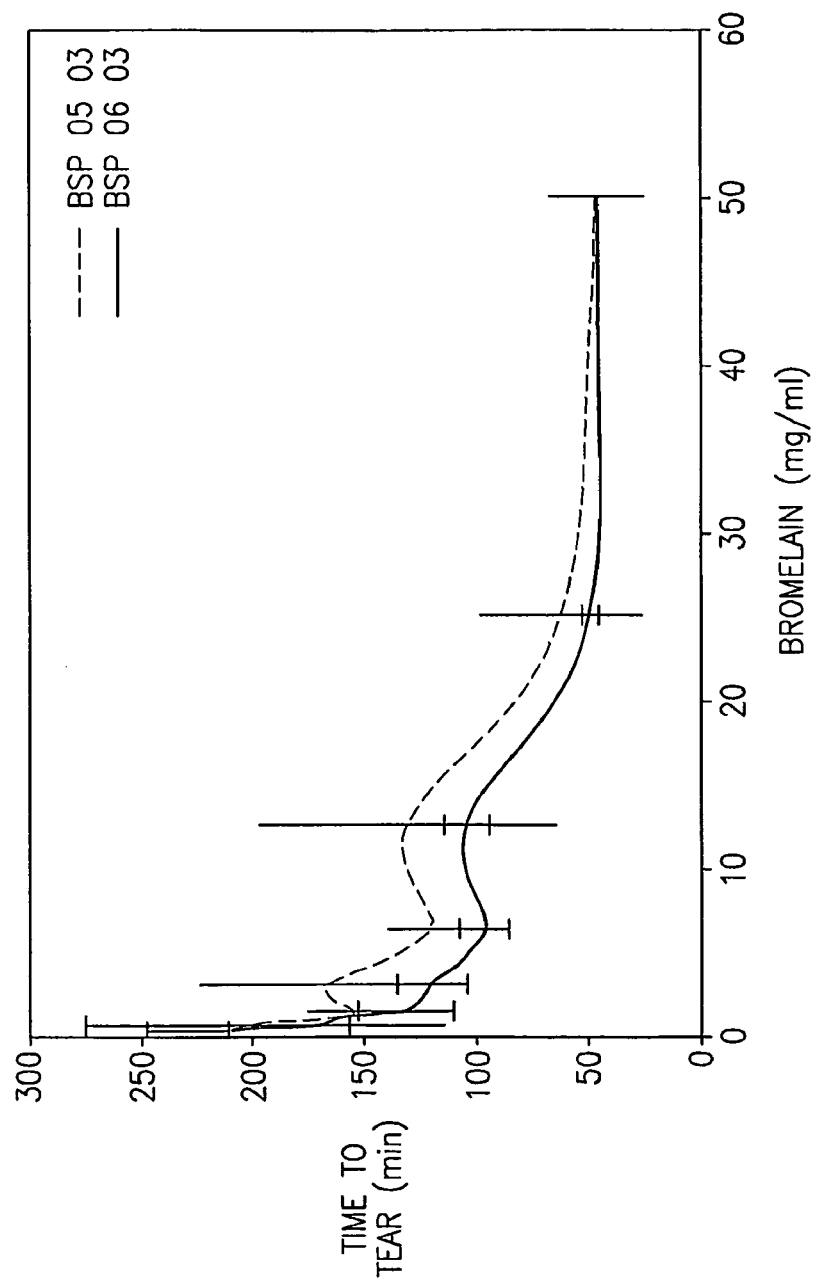
FIG. 5 shows the debriding activity of two preparations of bromelain on pig ear skin. The tear off time of pig ear skin pieces was measured as a function of bromelain concentrations.
Figure 6:
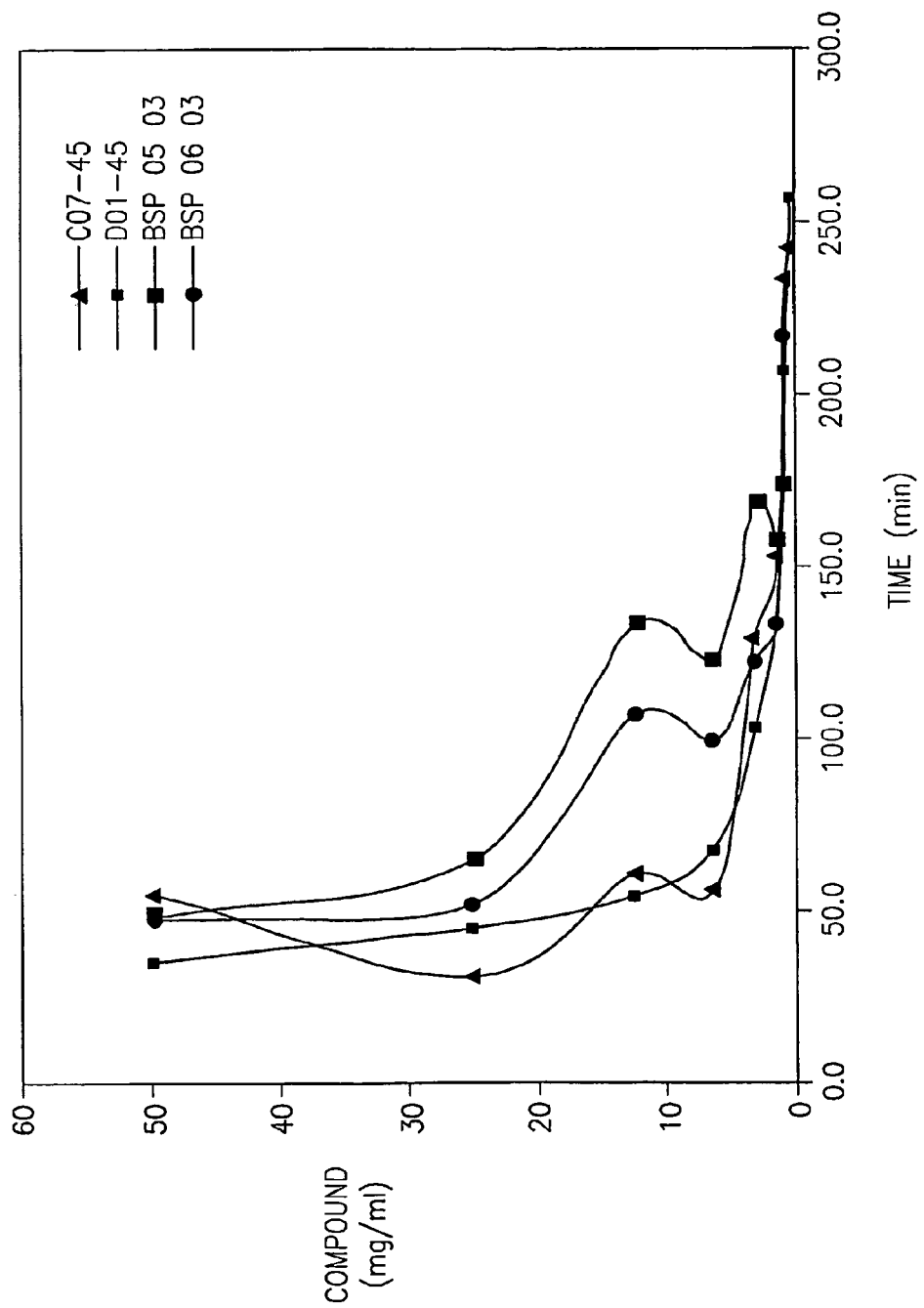
FIG. 6 shows the debriding activity of Debrase and bromelain on pig ear skin. The tear off time of pig ear skin pieces was measured as a function of Debrase and bromelain concentrations.

The results also show that Debrase is more efficient in tissue debridement at low concentrations than its starting material, bromelain (see FIG. 4 vs FIG. 5). As shown in FIG. 6, low (0-5 mg/ml) and high (20-50 mg/ml) concentrations of Debrase and bromelain exhibit similar tear off times. However, at concentrations of 5-20 mg/ml Debrase was shown to be twice as fast than bromelain in tearing pig ear skin.

It will be appreciated by persons skilled in the art that the present invention is not limited by what has been particularly shown and described herein above. Rather the scope of the invention is defined by the claims that follow.

What is claimed is:

1. A debriding composition obtained from bromelain, the debriding composition comprising a plurality of different proteolytic enzymes having molecular weights of about 23 kDa as determined by size exclusion chromatography, wherein the plurality of different proteolytic enzymes comprises:
   (a) stem bromelain comprising SEQ ID. No. 1;
   (b) ananain comprising SEQ ID No. 2;
   (c) stem bromelain comprising SEQ ID No. 3; and
   (d) cysteine proteinase precursor comprising SEQ ID No. 4, said debriding composition comprising bromelain inhibitors in an amount of less than 10% w/w of protein content of the debriding composition, wherein the composition consists essentially of a single protein peak after elution from an HPLC size exclusion column TSK-Gel $3000_{SWXL}$, the single protein peak constituting proteins having molecular weights of about 23 kDa.

2. The debriding composition according to claim 1 further comprising a pharmaceutically acceptable carrier.

3. A method of treating a wound by debriding non-viable tissues comprising applying a therapeutically effective amount of the debriding composition according to claim 1 to a wound.

4. The method of treating a wound according to claim 3, wherein the debriding composition further comprises a pharmaceutically acceptable carrier.

5. The method of treating a wound according to claim 3, wherein the wound is selected from the group consisting of full and partial thickness burn wounds, sunburns, frostbite, ulcerative lesions, pressure ulcers, varicose ulcers, stasis ulcers, trophic ulcers, wounds associated with surgical procedures, amputation, incision, circumcision and episiotomy, traumatic and pyogenic wounds, vaginitis, cervicitis, pilonidal cyst wounds, cataract scar tissue, and skin graft sites.

\* \* \* \* \*

SEQUENCE LISTING

<160> NUMBER OF SEQ ID NOS: 9

<210> SEQ ID NO 1
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 1

Ala Phe Glu Phe Ile Ile Ser Asn Lys Gly

```
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 2

Ile Asp Trp Arg Asp Ser Gly Ala Val Thr Ser
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 3

Tyr Pro Tyr Lys Ala Ala Lys Gly Thr Cys Lys Thr Asp Gly
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 4

Ser Arg Asp Glu Pro Ser Asp Pro Met Met Lys
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 5

Gln Asp Glu Tyr Lys Cys Tyr Cys
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 6

Cys Pro Gly Phe Cys Lys Thr Cys Lys Ala Glu
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 7

Cys Val Cys Ala Asp Thr Tyr Ser Asp Cys
1               5                   10
```

```
<210> SEQ ID NO 8
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 8

Ala Thr Val Glu Ser Ile Tyr Lys Gly Glu Ala Gly Tyr Ile Arg
1               5                   10                  15

<210> SEQ ID NO 9
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 9

Gly Ser Ser Trp Gly Glu Gly Gly Tyr Val Arg
1               5                   10
```